United States Patent
Buschke et al.

(10) Patent No.: US 6,641,535 B2
(45) Date of Patent: Nov. 4, 2003

(54) ULTRASONIC PROBE, IN PARTICULAR FOR MANUAL INSPECTIONS

(75) Inventors: Paul Buschke, Hürth (DE); Wolf Kleinert, Bonn (DE); Horst Guenter Thum, Köln (DE)

(73) Assignee: Agfa NDT GmbH (DE)

(*) Notice: Subject to any disclaimer, the term of this patent is extended or adjusted under 35 U.S.C. 154(b) by 0 days.

(21) Appl. No.: 10/380,306
(22) PCT Filed: May 12, 2001
(86) PCT No.: PCT/DE01/01814
§ 371 (c)(1), (2), (4) Date: Mar. 13, 2003
(87) PCT Pub. No.: WO02/42762
PCT Pub. Date: May 30, 2002

(65) Prior Publication Data
US 2003/0191388 A1 Oct. 9, 2003

(30) Foreign Application Priority Data
Nov. 22, 2000 (DE) .......................... 100 58 174

(51) Int. Cl.$^7$ ................................. A61B 8/00
(52) U.S. Cl. .................... 600/437; 600/445; 600/459
(58) Field of Search ........................ 600/407, 300, 600/409, 411–471; 73/625, 626; 367/7, 11, 130, 138; 128/916; 381/150, 173; 348/163

(56) References Cited

U.S. PATENT DOCUMENTS 4,774,842 A 10/1988 Kollar et al.
4,951,136 A 8/1990 Drescher et al.
5,690,110 A 11/1997 Tanaka
6,319,202 B1 * 11/2001 Inadama .................... 600/437

FOREIGN PATENT DOCUMENTS

GB 1 415 389 A 11/1975
GB 2 047 047 A 11/1980

\* cited by examiner

Primary Examiner—Ali M. Imam
(74) Attorney, Agent, or Firm—Akerman Senterfitt

(57) ABSTRACT

The invention relates to an ultrasonic probe comprising: —a housing (20), which accommodates an ultrasonic transducer and has a contact surface for making contact with the surface (28) of a body (30) to be inspected; —at least one digital camera (36), which is allocated to the housing (20) and which is aligned in such a way that it registers the surface (28) of the body (30) and supplies a respective electronic image of sub-sections of the surface (28) of the body (30) at intervals; —a circuit for image processing (40), which has an image memory (42) for at least one electronic image that has been registered by the digital camera (36). Said circuit also comprises a comparator (44) that compares two electronic images of the body (30) to be inspected, registered by the digital camera (36) at different times and that determines the displacement of the housing (20) in relation to the surface (28); and a displacement memory (46), which contains the displacement of the housing (20) and the current position of the housing (20) in relation to the original location (48).

12 Claims, 2 Drawing Sheets

ULTRASONIC PROBE, IN PARTICULAR FOR MANUAL INSPECTIONS

Figure 1:
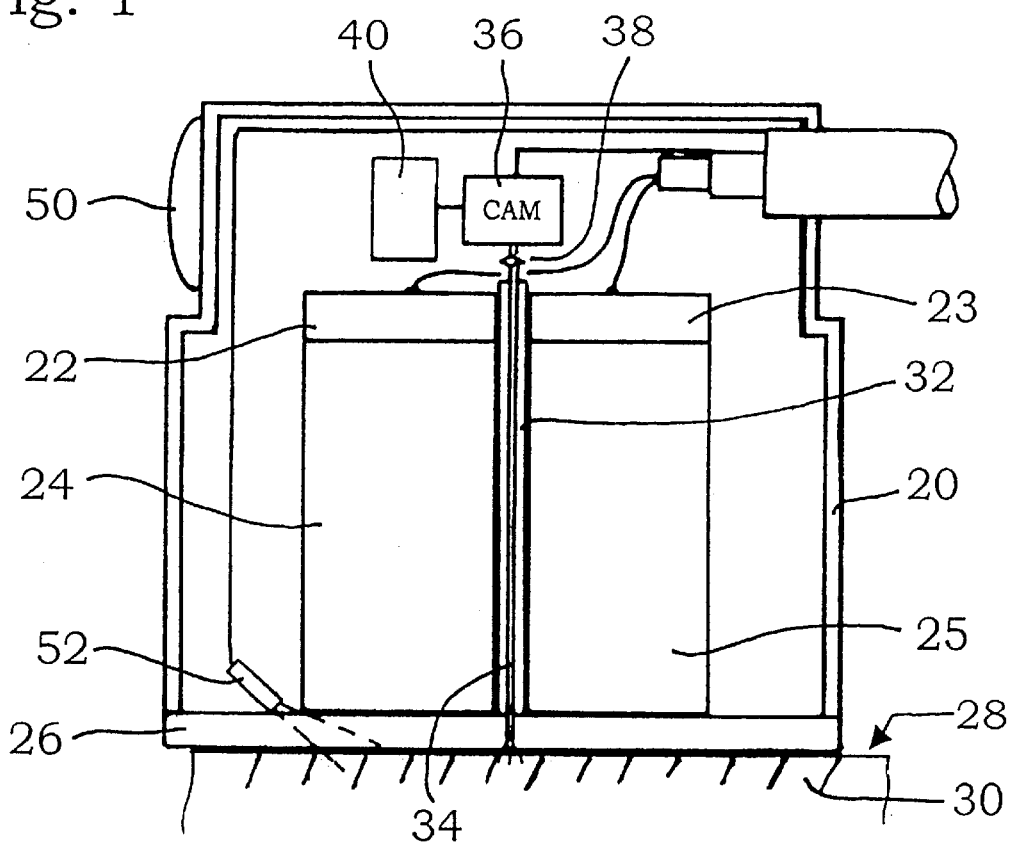

The invention relates to an ultrasonic probe, more specifically for manual inspection. It has a housing which accommodates an ultrasonic crystal and has a contact surface for contact with the surface of a body to be inspected.

Extensive prior art exists with respect to such type ultrasonic probes. In ultrasonic inspection one would like to know with the greatest possible accuracy the location on the body to be inspected that corresponds to the ultrasonic test results. Meaning, one would like to associate an ultrasonic test result with a corresponding location. As a result, one aims at being capable of accurately localizing a detected flaw during weld testing. In the same way, it is also desirable to exactly know the location on the container or pipe at which a predetermined ultrasonic test result was determined during determination of remaining wall thickness of a tube or a container. This means that not only the ultrasonic signal is to be known, but the respective position of the ultrasonic probe on the surface of the body to be inspected as well.

According to prior art, systems exist that determine the position of the ultrasonic probe, e.g., as a position of the probe in two or three axes relative to a location, as the measurement is being started. For the time being, a resolution of 0.1 mm is achieved for longitudinal movements and 0.1° for rotational movements. Together with the relative position data and the respective ultrasonic test result the absolute position of a flaw may be determined with accuracy. As a result, repair work or systematic monitoring of defective sites may be performed profitably and selectively.

The currently used methods of determining the position data in manual ultrasonic inspection have some major disadvantages. For detecting the position, additional electronic component parts such as e.g., airborne sound sensors and/or mechanical guides are needed, which have ergonomic drawbacks. The mechanical parts may wear, the airborne sound sensors are relative large in size, more specifically to install and to adjust. The cost of the known methods and of the devices used for this purpose is high.

In view thereof it is an object of the present invention to produce an ultrasonic probe that ascertains and outputs position coordinates on the body to be inspected as a function of a location known as measurement starts. The disadvantages of the hereto before known systems are to be avoided.

The solution to this object is an ultrasonic probe, more specifically for manual inspection
- with a housing that accommodates an ultrasonic crystal and has a contact surface for contact with the surface of a body to be inspected,
- with at least one digital camera that is assigned to the housing, is oriented in such a manner that it acquires the surface of the body and periodically delivers an electronic image of respective portions of the body's surface,
- with a circuit for image processing that is comprised of an image memory for at least one electronic image acquired by the digital camera, that has a comparator which compares two electronic images, acquired at different times by the digital camera, of overlapping portions of the body's surface and determines therefrom the displacement of the housing relative to the surface, which is then output, and
- with a motion memory that stores the displacement of the housing starting from a location at the beginning of the measurement and contains the actual position of the housing with respect to said location.

To begin with, this ultrasonic probe is a classical ultrasonic probe having the usual features of a such type probe. By way of example the reader is referred to the DE-book J. Krautkrämer & K. Krautkrämer "Werkstoffprüfung mit Ultraschall" ("Material Inspection with Ultrasounds"), $6^{th}$ edition, Springer-Verlag. Accordingly, the ultrasonic probe may be utilized like a conventional ultrasonic probe. It is for example configured as a double transducer probe.

In addition, the ultrasonic probe in accordance with the invention has means serving to indicate the respective position on the surface of the body to be inspected with regard to a location that was known at the beginning of the measurement.

For this purpose, at least one digital camera is firmly connected to the housing. The digital camera is preferably disposed in the housing. It is oriented so as to acquire the surface of the body to be inspected. It is thereby to deliver an image of this surface in the nearest possible proximity to the site at which a central beam of the active sound element traverses the surface.

By means of this digital camera, an electronic image (frame) is periodically acquired of that surface portion that is just located beneath the lens of the digital camera, meaning that lies in the plane of the object. This portion is a relatively small portion of the overall surface of the body to be inspected. The portion may have dimensions of a few mm, e.g., 2×2 to 4×4 mm. At predetermined fixed time intervals, the digital camera preferably takes an image of the respective one of the surface portions.

In the circuit for image processing connected downstream the digital camera, at least one image taken with the digital camera is stored in an image memory. In the comparator this image is compared with an image the digital camera acquired later. The comparator displaces the two electronic images to find a match with each other, meaning until corresponding image zones are coinciding. This means that the interval of time between two electronic images to be compared being taken is not allowed to be greater than the time during which the housing is displaced by a distance that is greater than the diagonal of the acquired electronic image. In this case the electronic images to be compared do not contain any matching portions any longer so that comparison is not possible.

The actual displacement on the surface of the body to be inspected may be computed from the necessary relative displacement of the two individual images compared in the comparator to find a match with each other. The image scale of the optics is substantially taken into consideration in this computation. Accordingly, a position signal may be delivered that is indicative of the displacement of the probe between the time at which the first electronic image was taken and the time at which the second electronic image was taken. The respective actual position of the probe on the surface of the body to be inspected is obtained from the sum of the individual displacement information data starting from the location at the beginning of the measurement.

Accordingly, an optical system forms the basis for position detection. The digital cameras are preferably equipped with CCD sensors. The object field of the digital camera is preferably assigned a lighting element for illuminating the surface portion to be acquired. Upon motion of the probe, the actual position is determined from the position information data contained in the motion memory.

Nowadays, the electronic and optical means utilized for determining the position are available in very small sizes and at low cost as well. As a result, the complete image evaluation unit may be accommodated within a housing of a conventional ultrasonic probe. More specifically, with the ultrasonic probe of the invention, the evaluation of spatially small flaws may be carried out parallel to the surface of the body to be inspected. In testing welds such as in tubes, pipelines or in the construction of containers and boilers, the locations of the respective sites may be indicated in a test result.

The use of double transducer probes allows for simplified application in determining location coordinates. The transmit/receive crystal of the ultrasonic probe is separately accommodated within a housing, the separation being provided by an attenuation web. At least one digital camera permits to determine in the simplest manner the position of two axes specifically for these probes. The remaining wall thickness of curved tubes may thus be determined advantageously.

The distance travelled is summed in the motion memory. Inspections may thus be performed profitably, with enhanced ergonomics. An inspector guiding the probe may perform the test at optimum conditions. No parts are subject to wear and inspection safety is considerably increased as compared to inspection without additional information concerning the location coordinates. As compared to mechanical systems for position acquisition, costs are saved up to 60%. Exhaustive documentation of the inspection is possible.

In a particularly preferred development, two digital cameras are provided, said cameras being spaced apart on the housing, each of them having a circuit for image processing of its own connected downstream thereof, and being provided with an evaluation step for rotations at which the outputs of the two circuits for image processing are applied. A rotation of the housing relative to a previous rotational condition is determined from the various information about the position of the housing obtained from said two circuits for image processing and is output. A rotation memory contains the rotation information starting from a rotational condition at the beginning of the measurement.

When two digital cameras are being used, the position of the angle of rotation of the probe about its own axis may be very easily determined by way of transformation functions. Although it would be possible in principle to acquire this position with only one camera as well, this would require the image comparison within the comparator to be performed in such a manner that the electronic images are not only displaced in pixel bounds relative to one another in but two directions until a match is achieved for a partial region thereof, but that the two compared electronic images are also rotated relative to each other. This considerably increases the expense and time needed for the electronic evaluation in the comparator. Inasmuch, to install a second digital camera is a simple and advantageous solution.

In the embodiment with two digital cameras, there is provided a rotation memory that stores the determined rotation information starting from the condition at the beginning of the measurement. In this way, the respective overall rotation as compared to the condition at the beginning of the measurement is known.

In a preferred development there is provided a signal memory which is permanently assigned to the motion memory and which stores the ultrasonic information available at a respective position together with the position information. The result of the ultrasonic inspection may thus be readily accessed. An evaluation may be performed in different ways. It is thereby particularly preferred if, whenever a critical ultrasonic inspection test result is obtained, e.g., whenever a preset threshold is exceeded in the signal, this condition is shown on a display. Defective sites and other imperfections in the body to be inspected are thus displayed on a monitor for example. The information obtained may thus be readily processed further.

A start switch proved very advantageous. It is preferably disposed on the housing of the ultrasonic probe. It may concurrently be assigned various functions that are independent of each other. Upon actuation of the start switch, the motion memory is reset and restarts summing up the subsequently delivered motion information. The start switch may also serve to start the optical and electronic unit for position acquisition. As a result thereof, said unit may be in a low-current off function before that. Also, the lighting means may be switched off.

It is possible but not necessary to provide a coupling means, water for example, between the ultrasonic probe and the surface of the body to be inspected. The function of optical position detection proved not to be affected thereby.

Figure 2:
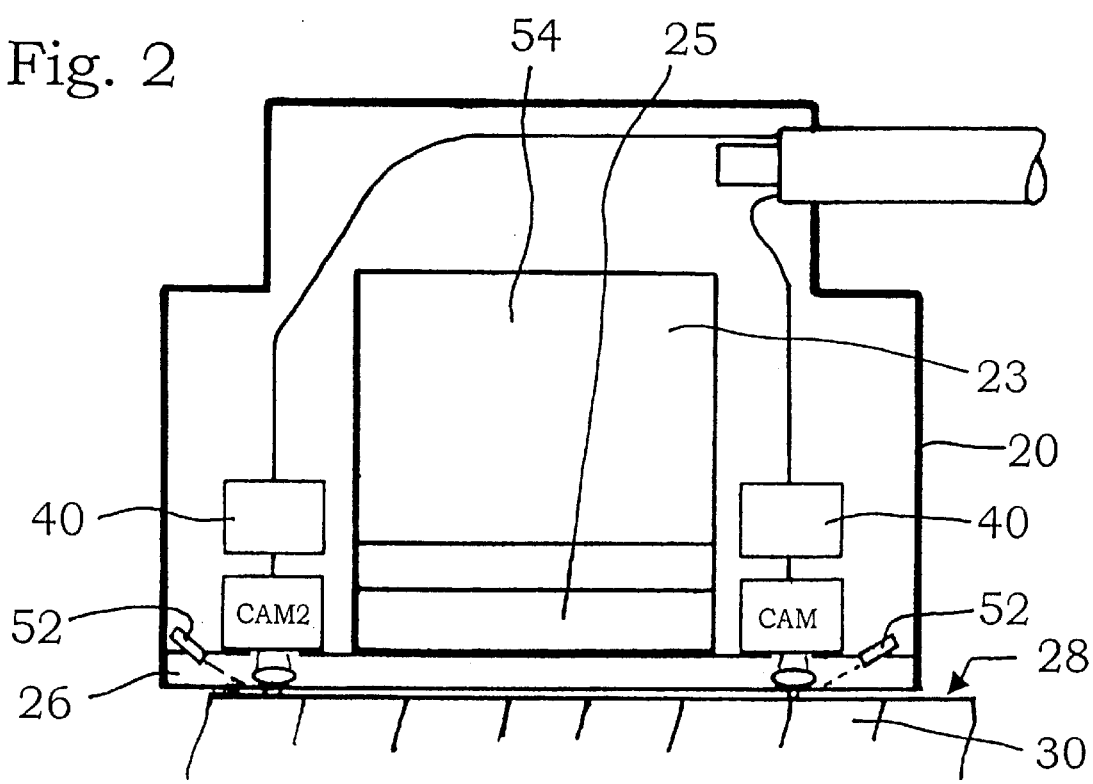
Figure 3:
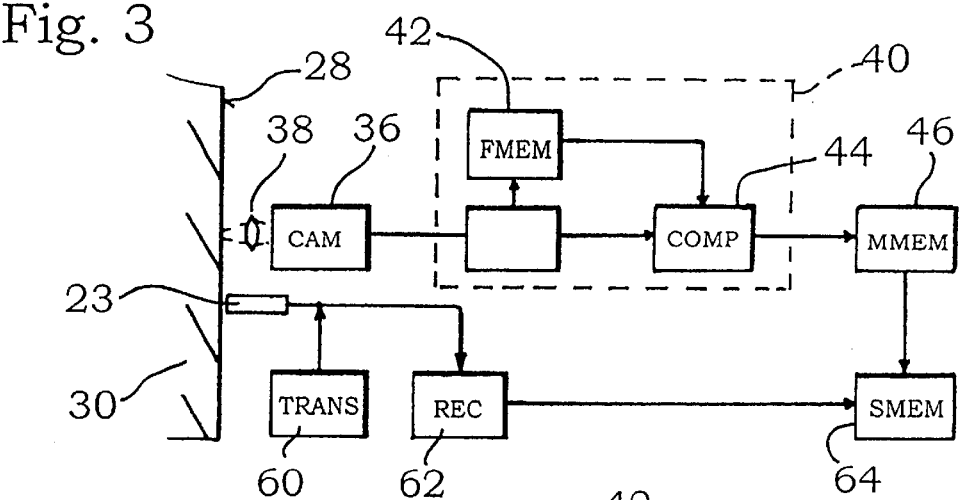
Figure 4:
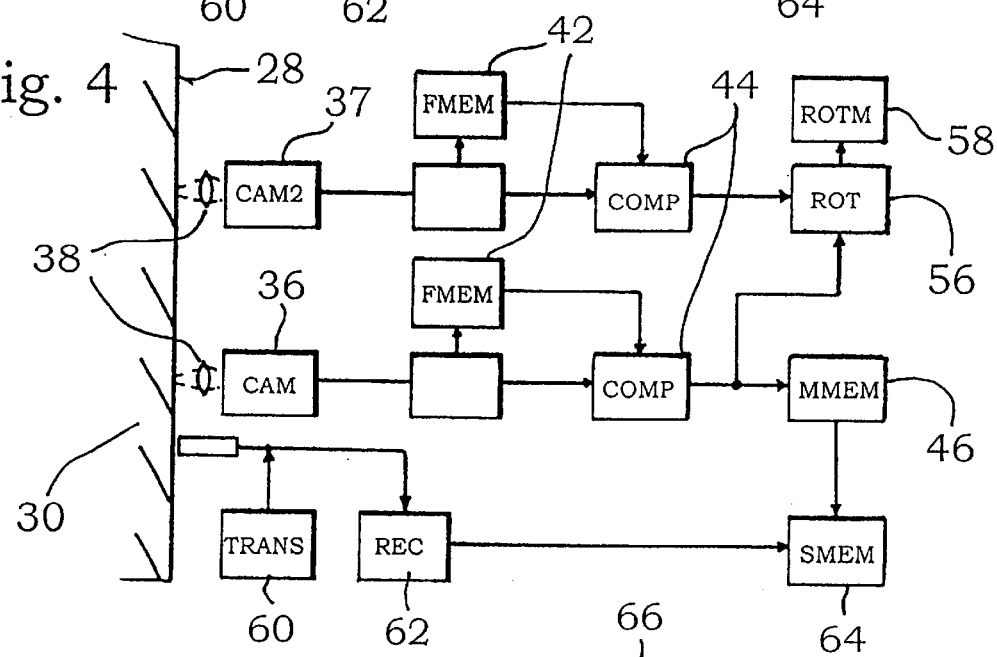
Figure 5:
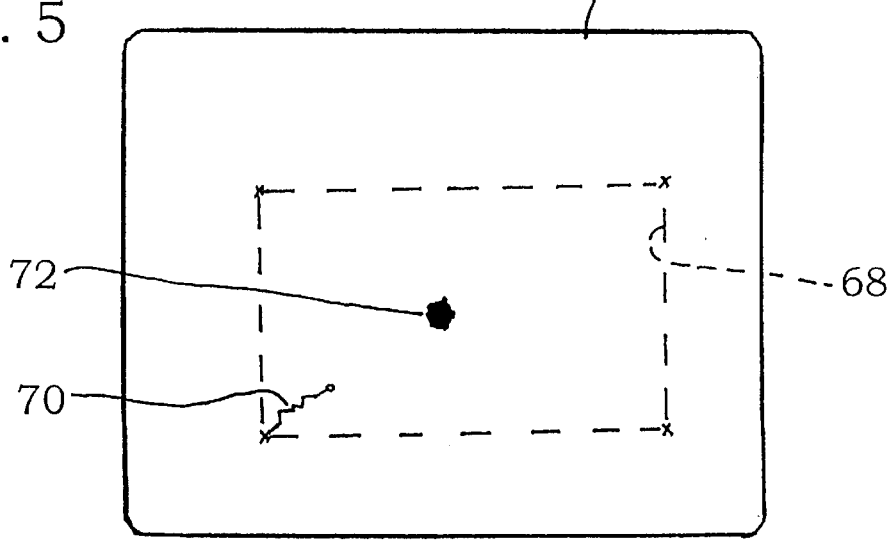

Further advantages and characteristics of the invention will become apparent in the remaining claims and in the following non restrictive description of embodiments given by way of example only with reference to the drawings in which:

FIG. 1 is a schematic representation of a side view of an ultrasonic probe, configured as a double transducer probe, FIG. 2 is a representation of an ultrasonic probe similar to that in FIG. 1, but this time with two digital cameras, FIG. 3 is a block diagram for an ultrasonic probe similar to that in FIG. 1, FIG. 4 is a block diagram for an ultrasonic probe similar to that in FIG. 2, FIG. 5 is a representation of a monitor reproducing a body to be inspected which has a defective site.

The ultrasound probes are intended for use in nondestructive inspection of materials. Inspection is performed according to the pulse echo method. The ultrasonic probe according to the FIGS. 1 and 3 has a housing 20 for receiving ultrasonic crystals. One transmit crystal 22 and one receive crystal 23 are shown. The transmit crystal 22 is placed on a leading body 24, the receive crystal 23 is placed on a leading body 25. The two leading bodies 24, 25 are located on a protective body 26 forming a leading and a protective layer. Said protective body 26 contacts a surface 28 of a body to be inspected 30. The protective body 26 is made from a transparent, preferably clear material such as an acrylic material. A lower, freely accessible area of the protective body 26 forms the contact surface for contacting the housing 20 with the surface 28 of the body to be inspected 30.

As it is often the case with double transducer probes, there is provided an attenuation web 32 between the transmit crystal 22 and its leading body 24 on the one side and the receive crystal 23 and its leading body 25 on the other side, said attenuation web forming a spacer piece. Said web has a hole through which an optical fiber 34 is passed. A bundle of optical fibers may also be used instead of but one optical fiber. The optical fiber 34 ends within the protective body 26 and in proximity to the surface 28 onto which it is directed (see dashed lines). It transmits the image of a small portion of the surface 28 to a digital camera 36 located within housing 20. It is also referred to as CAM. The digital camera used is an optical reflective sensor HDNS-2000 of HP. It is assigned a lens 38 that is available from the same company and sold by the designation HDNS-2100. Other digital cameras may also be utilized.

The digital camera 36 has a light-sensitive array which is more specifically configured as a CCD and is provided with a plane array (matrix) of pixels. The lens 38 maps the portion of the surface 28 considered onto this array.

Periodically, the digital camera 36 acquires electronic images, which will also be termed frames herein after, of the portion of surface 28 considered. Typically, a frame is acquired every 8 ms.

A circuit for image processing 40 is connected downstream of the digital camera 36. It has an image memory 42 which is also termed FMEM and is suited for at least one frame acquired by the digital camera 36. This frame more specifically is the penultimate frame acquired by the camera and stored in the image memory 42. In a comparator 44, which is also indicated at COMP, this frame is compared with the actual frame. The two frames are displaced pixel by pixel parallel to the rows and lines of pixels to find a match of image zones of the frame. This is only possible on the condition that the frames contain overlapping portions of the surface of the body to be inspected 30. The displacement in the plane of the object, meaning on the surface 28 of the body to be inspected 30, may then be calculated from the displacement of the two frames in the image plane of the digital camera 36. The imaging ratio of the digital camera 36, its lens 38 inclusive, is thereby substantially to be taken into consideration.

As a result, the circuit 40 for image processing transmits the information about the displacement of housing 20 between the times at which the two compared frames were acquired to a motion memory which is also termed MMEM. The motion memory 46 continuously stores the displacements it receives. The displacements are transformed into x-values and y-values and are entered in a rectangular coordinate system. The actual position of housing 20 is thus always contained in the motion memory 46.

In the motion memory 46, the movements starting from a location 48 occupied by the housing at the beginning of the measurement are summed up. The start of the measurement is entered by a start switch 50. Upon actuation of the start switch 50, the motion memory 46 is at first reset or brought to zero. It then stores all the motion information it receives, meaning the increments in the two directions. The information of the motion memory 46 may be displayed on a monitor 52; this will be discussed herein after.

As shown in FIG. 1, the portion of the surface 28 considered is illuminated by a lighting means 52 which in this case is configured as an LED. The surface 28 is preferably illuminated from the side in order for the digital camera 36 to be capable of acquiring as many contours as possible. It is advantageous to only switch on the lighting means 52 upon actuation of the start switch 50. When a complete match is found for some consecutive frames and when, as a result thereof, no motion of housing 20 is detected, the circuit 40 is switched into a low current mode.

As shown in FIG. 1, the lighting means 52 is disposed within housing 20 in such a manner that the transparent protective body 26 is radiated through. It may also be accommodated within the protective body 26. If a coupling means is to be used between protective body 26 and surface 28, a completely transparent means such as water is preferably used.

In contrast to the embodiment of the probe according to the FIGS. 1 and 3, the probe according to the FIGS. 2 and 4 has two digital cameras 36 and 37, also see CAM and CAM 2. They are held apart from each other within housing 20 and are in fact positioned on either side of a crystal 23. This crystal 23, which may also be a transmit crystal, is assigned an attenuation body 54 rearward therefrom. In the direction of sound propagation there is provided a leading body 25 which in turn contacts a protective body 26.

The arrangement of two digital cameras 36, 37 and of two lighting means 52 substantially corresponds to twice the arrangement according to FIG. 1. In contrast to the embodiment according to FIG. 1, it is no longer an optical fiber that is used to transmit the image of a portion of surface 28 to the digital camera 36, the respective lenses 38 of the digital cameras 36, 37 are instead accommodated within the protective body 26. They may also be placed on its upper surface or in proximity thereto.

The additional function obtained by the second digital camera 37, also termed CAM 2, will be explained herein after with reference to FIG. 4. This Fig. shows the two digital cameras 36, 37, a circuit 40 for image processing being connected downstream of a respective one of said cameras. The surface 28 of body 30 is shown. A respective portion of this surface is acquired, the portions are spaced apart. At the output of the respective one of the circuits 40 for image processing, the information about the position increments of every single digital camera 36, 37 is available. This information is now processed as follows: to determine the position, only the digital camera 36, which is the lower one in FIG. 4, is used and inasmuch there is no difference as compared to FIG. 2. The upper digital camera 37 is only used to deliver, in connection with the lower digital camera 36, an information about the rotation of housing 20. For this purpose, the displacement information data of the two circuits 40 for image processing are forwarded to an evaluation step 56, also termed ROT. There, the different increments are compared and the respective rotation of housing 20 that may be ascertained between the frames considered is determined. A rotation memory 58, also termed ROTM, is connected downstream of said evaluation step 56. This is where the rotational condition of housing 20, starting from the condition at location 58 at the beginning of the measurement, is stored.

As already explained, the digital cameras 36, 37 acquire frames every 8 ms. Next, the images are evaluated. Very little time is needed therefore, the images are evaluated in less than 1 ms. Short image evaluation is achieved in that, in the comparator step 44, the frames to be compared need only be displaced pixel by pixel in the direction of the rows and lines of pixels. The frames are not rotated relative to each other. In principle however, the individual frames may also be rotated relative to each other in the comparator 44. Then, a second digital camera 37 is not needed.

The FIGS. 3 and 4 also show an ultrasonic array. A crystal 23 is shown without any additional body. It is connected to a transmitter 60, also indicated at TRANSM, on the one hand and to a receiver 62, also indicated at REC, on the other hand. A memory 64, also designated with SMEM, is connected downstream of the receiver 62. Said memory 64 is also connected to the motion memory 46. The ultrasonic test result obtained from the receiver 62 after evaluation and the respective position at which this ultrasonic test result was obtained are stored in memory 64. The respective position relates to location 48.

In an advantageous development, the ultrasonic probe is assigned a device for determining the position such as a circuit for global positioning according to the GPS method. In this way, the absolute value of location 48 known at the beginning of the measurement is determined. This absolute determination is recorded in the motion memory 46 or in memory 64.

FIG. 5 is a representation of an ultrasonic measurement performed with the ultrasonic probe in accordance with the invention and displayed on a monitor 66. An ultrasonic flaw detector of the applicant of the type USD 15 with a crystal array with leading body and so on of the type CLF 4 which was additionally fitted with the device for determining the position according to the invention, meaning with a structure as shown in FIG. 1, was used.

The workpiece to be tested, that is the body 30, was a rectangular steel plate. A bore of a diameter of 3 mm and a depth of 2.5 mm was drilled therein. The aperture of the instrument USD 15 was adjusted as follows: beginning 2 mm, width 1 mm. As a result, the bore had to deliver a flaw signal.

At first, the probe was positioned on a corner of the body 30. Then, the start switch 50 was pressed and the probe was moved to a neighbouring corner. This was repeated until the periphery of the body 30 was scanned. Thus, the contour 68 displayed in dashed lines on the monitor 66 was obtained.

The location 48 chosen for the beginning of the measurement was the lower left corner of the body 30. There, the start switch 50 was actuated. The beginning of the inspection is schematically shown by a path 70. The complete inspection path on which the probe was guided over the surface 28 of body 30 is not shown. It may be shown, though. But, in this specific case, this would affect the readability of the drawing. In FIG. 5, an information in writing was only delivered to the monitor 66 or to the computer connected upstream thereof when the instrument USD 15 delivered a flaw signal. As a result, when the bore was scanned, short black dashes were written, which all together give an image 72 of the flaw. An approximately circular, black spot is to be seen. In this way, the flaw may be accurately localized.

What is claimed is:

1. An ultrasonic probe for manual inspection of a body, comprising:

a housing that accommodates an ultrasonic crystal and has a contact surface for contact with a surface of the body to be inspected;

at least one digital camera that is attached to the housing and which is oriented towards the surface of the body and periodically delivers an electronic image of portions of the surface of the body;

a circuit for image processing that has an image memory for at least one electronic image acquired by the digital camera, and which has a comparator which compares two electronic images, acquired at different times by the digital camera, of overlapping portions of the surface of the body to be inspected and which determines from differences of these two electronic images a displacement of the housing relative to the surface, which is then output; and a motion memory that stores the displacement of the housing starting from a location at the beginning of the measurement and contains the actual position of the housing with respect to said location.

2. The ultrasonic probe according to claim 1, comprising:

two of said digital cameras the digital cameras being spaced apart, each digital camera having a circuit for image processing of its own, each circuit for image processing having an output;

an evaluation circuit for evaluating a rotation and coupled with the outputs of the two circuits for image processing the evaluation circuit determining, from information about the position of the housing obtained from the two circuits for image processing, a rotation of the housing relative to a previous rotational condition, the rotation being output; and a rotation memory that contains the rotation information starting from a rotational condition at the beginning of the measurement.

3. The ultrasonic probe according to claim 1, further comprising a lighting means oriented to illuminate the region of the surface of body seen by the digital camera.

4. The ultrasonic probe according to claim 3, wherein the lighting means is disposed in the housing.

5. The ultrasonic probe according to claim 3, wherein the rays of the lighting means impinge upon the surface of body at the shallowest angle possible.

6. The ultrasonic probe according to claim 1, wherein a start switch is provided wherein an actuation of the start switch clears the motion memory and stores the present location as being a new starting location for further movement.

7. The ultrasonic probe according to claim 1, further comprising a protective body having a freely accessible outer face forming the contact surface of the housing.

8. The ultrasonic probe according to claim 7, wherein the protective body is transparent.

9. The ultrasonic probe according to claim 7, wherein the protective body is clear and transparent.

10. The ultrasonic probe according to claim 7, wherein the protective body is made from an acrylic material.

11. The ultrasonic probe according to claim 7, wherein the at least one digital camera is disposed on the inner side of the protective body.

12. The ultrasonic probe according to claim 1, wherein the at least one digital camera is accommodated in the housing.

* * * * *